(12) United States Patent
Jung et al.

(10) Patent No.: US 12,365,647 B2
(45) Date of Patent: Jul. 22, 2025

(54) METHOD FOR PREPARING ACRYLONITRILE DIMER

(71) Applicant: LG CHEM, LTD., Seoul (KR)

(72) Inventors: Hyun Chul Jung, Daejeon (KR); Sae Hume Park, Daejeon (KR); Won Seok Kim, Daejeon (KR); Ji Ha Kim, Daejeon (KR); Young Shil Do, Daejeon (KR); Yu Jin An, Daejeon (KR); Wan Kyu Oh, Daejeon (KR); Jeong Heon Ahn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 940 days.

(21) Appl. No.: 17/606,711

(22) PCT Filed: Jan. 5, 2021

(86) PCT No.: PCT/KR2021/000049
§ 371 (c)(1),
(2) Date: Oct. 26, 2021

(87) PCT Pub. No.: WO2021/145598
PCT Pub. Date: Jul. 22, 2021

(65) Prior Publication Data
US 2022/0204440 A1 Jun. 30, 2022

(30) Foreign Application Priority Data

Jan. 13, 2020 (KR) .......... 10-2020-0004079
Dec. 17, 2020 (KR) .......... 10-2020-0177058

(51) Int. Cl.
*C07C 253/30* (2006.01)
*B01D 3/14* (2006.01)
*B01J 31/02* (2006.01)
*C07C 253/34* (2006.01)

(52) U.S. Cl.
CPC ............ *C07C 253/30* (2013.01); *B01D 3/143* (2013.01); *B01J 31/0262* (2013.01); *C07C 253/34* (2013.01)

(58) Field of Classification Search
CPC ..... C07C 253/30; C07C 253/34; B01D 3/143; B01J 31/0262
See application file for complete search history.

(56) References Cited

U.S. PATENT DOCUMENTS

| | | | |
|---|---|---|---|
| 4,102,915 A | 7/1978 | Jennings et al. | |
| 4,126,632 A | 11/1978 | Hogan et al. | |
| 4,841,087 A | 6/1989 | Mathews, III et al. | |
| 4,958,042 A | 9/1990 | Shaw et al. | |
| 6,559,332 B1 | 5/2003 | Gurtler et al. | |
| 7,692,007 B2 | 4/2010 | Ignatyev et al. | |
| 2008/0027230 A1 | 1/2008 | Ignatyev et al. | |

FOREIGN PATENT DOCUMENTS

| | | |
|---|---|---|
| CN | 1984893 A | 6/2007 |
| CN | 105837470 A | 8/2016 |
| CN | 108517536 B | 6/2019 |
| EP | 0314383 A1 | 5/1989 |
| FR | 2351093 A1 | 12/1977 |
| GB | 547 431 A | 6/1979 |
| JP | S51-88918 A | 8/1976 |
| JP | S52-057122 A | 5/1977 |
| JP | 5-286918 A | 11/1993 |
| JP | H06-122638 A | 5/1994 |
| JP | 2888392 B2 | 2/1999 |
| JP | 2008506641 | 3/2008 |
| JP | 2012-133003 A | 7/2012 |
| KR | 10-1409542 B1 | 6/2014 |
| KR | 10-2017-0116045 A | 10/2017 |
| WO | 93/10082 A1 | 5/1993 |

OTHER PUBLICATIONS

Noh, "A Study on the Pressure-Swing Distillation of Ethanol-n-Heptane Azeotrope," Clean Technology, vol. 21. No. 4, Dec. 2015, pp. 217-223.
Chemistry of Makoto Takeda, Mitsuo Minafuji, and 2-MethyleneGlutaronitrile, Society of Synthetic Organic Chemistry, Japan, Sep. 1, 1981, 39th vol. No. 9, pp. 813-824.

*Primary Examiner* — Sikarl A Witherspoon
(74) *Attorney, Agent, or Firm* — BRYAN CAVE LEIGHTON PAISNER LLP

(57) ABSTRACT

Provided is a method of preparing an acrylonitrile dimer, the method including: supplying an acrylonitrile monomer, a phosphorus-based catalyst, an alcohol solvent, and an ionic liquid to a reactor to perform a dimerization reaction to prepare a single-phase dimerization reaction product (S10); supplying a reactor discharge stream including the dimerization reaction product to a first distillation column, separating the alcohol solvent and an unreacted acrylonitrile monomer from an upper discharge stream, and supplying a lower discharge stream including an acrylonitrile dimer, the ionic liquid, and the phosphorus-based catalyst to a second distillation column (S20); and separating an upper discharge stream including the acrylonitrile dimer and separating a lower discharge stream including the ionic liquid and the phosphorus-based catalyst, from the second distillation column (S30).

9 Claims, 1 Drawing Sheet

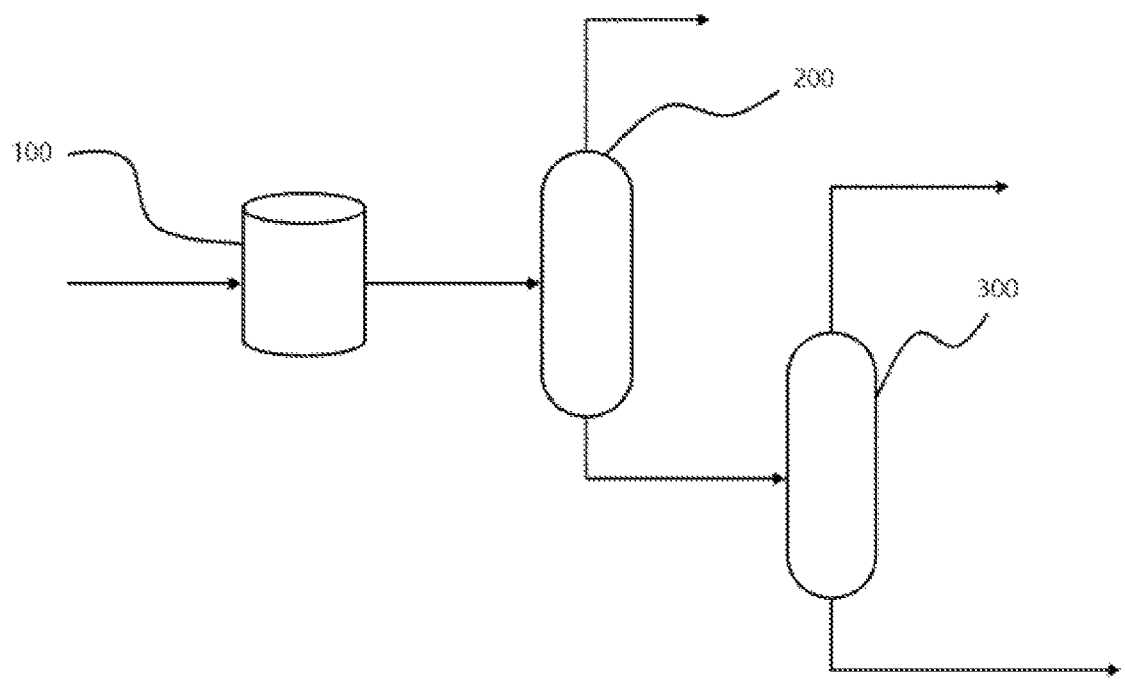

METHOD FOR PREPARING ACRYLONITRILE DIMER

CROSS-REFERENCE TO RELATED APPLICATIONS

The present application is a National Phase entry pursuant to 35 U.S.C. § 371 of International Application No. PCT/KR2021/000049, filed on Jan. 5, 2021, and claims the benefit of and priority to Korean Patent Application No. 10-2020-0004079, filed on Jan. 13, 2020, and Korean Patent Application No. 10-2020-0177058, filed on Dec. 17, 2020, the entire contents of which are incorporated by reference in their entirety for all purposes as if fully set forth herein.

TECHNICAL FIELD

The present invention relates to a method of preparing an acrylonitrile dimer, and more particularly, to a method of preparing a high yield of a linear acrylonitrile dimer by effectively separating a phosphorus-based catalyst used as a catalyst, in an acrylonitrile dimerization reaction.

BACKGROUND ART

An acrylonitrile dimer, in particular, a linear acrylonitrile dimer, is used as an intermediate for synthesizing hexamethylenediamine (HMDA) which is a main monomer of Nylon 66 or for the preparation of a waterproof agent, a vulcanization accelerator, and the like.

The acrylonitrile dimer may be obtained by a method of dimerizing an acrylonitrile monomer in the presence of a catalyst. Specifically, the acrylonitrile monomer may be dimerized using a ruthenium (Ru)-based compound, a cobalt (Co)-based compound, a phosphorus (P)-based compound, or the like as a catalyst, thereby preparing an acrylonitrile dimer.

A method of preparing an acrylonitrile dimer using a ruthenium-based compound among the catalysts has been mainly studied, and due to an addition of hydrogen for causing a dimerization reaction, a yield of an acrylonitrile dimer and selectivity of a linear acrylonitrile dimer were lowered. That is, as hydrogen is added, hydrogenation occurs together with a dimerization reaction of acrylonitrile to produce a large amount of propionitrile as a by-product, thereby lowering a yield and selectivity.

Accordingly, in order to increase the yield of an acrylonitrile dimer, a method of preparing an acrylonitrile dimer using a phosphorus-based compound as a catalyst receives attention. As the method of preparing an acrylonitrile dimer using a phosphorus-based compound as a catalyst, there is a method of adding acrylonitrile to a mixed solvent including an alcohol solvent as a proton donating solvent and an inert solvent such as an aromatic hydrocarbon solvent as a reaction solvent in the presence of the phosphorus-based catalyst and performing a dimerization reaction.

However, the method has a problem in that it is difficult to separate the phosphorus-based catalyst, the acrylonitrile dimer, and the mixed solvent due to an azeotropic problem of the alcohol solvent and the aromatic hydrocarbon solvent, thereby lowering a recycling rate of the catalyst and the yield of the acrylonitrile dimer.

In addition, separation of the phosphorus-based catalyst, the acrylonitrile dimer, and the mixed solvent is performed by a distillation method, and the distillation method is a method of separating a catalyst by applying heat using the characteristic of the phosphorus-based catalyst having a higher boiling point than a reaction product or a product, and when the catalyst is separated from the acrylonitrile dimerization reaction product by the distillation method, a side reaction of the acrylonitrile dimerization products proceeds by heat to produce an acrylonitrile trimer, a polymer, and the like to lower the yield of the acrylonitrile dimer.

Accordingly, a technique for both increasing a yield of the acrylonitrile dimer and a recycling rate of the phosphorus-based catalyst is demanded.

DISCLOSURE

Technical Problem

An object of the present invention is to provide a method of easily separating a phosphorus-based catalyst from an acrylonitrile dimerization reaction product and preparing a high yield of an acrylonitrile dimer, in order to solve the problems mentioned in the Background Art.

That is, the present invention uses an ionic liquid as a reaction solvent in the preparation of the acrylonitrile dimer, thereby solving a problem of making it difficult to recover a phosphorus-based catalyst in the conventional preparation of an acrylonitrile dimer using a phosphorus-based catalyst, which results in a yield decrease of the acrylonitrile dimer.

Technical Solution

In one general aspect, a method of preparing an acrylonitrile dimer includes: supplying an acrylonitrile monomer, a phosphorus-based catalyst, an alcohol solvent, and an ionic liquid to a reactor to perform a dimerization reaction to prepare a single-phase dimerization reaction product (S10); supplying a reactor discharge stream including the dimerization reaction product to a first distillation column, separating the alcohol solvent and an unreacted acrylonitrile monomer from an upper discharge stream, and supplying a lower discharge stream including an acrylonitrile dimer, the ionic liquid, and the phosphorus-based catalyst to a second distillation column (S20); and separating an upper discharge stream including the acrylonitrile dimer and separating a lower discharge stream including the ionic liquid and the phosphorus-based catalyst, in the second distillation column (S30).

Advantageous Effects

According to the method of preparing an acrylonitrile dimer, when preparing an acrylonitrile dimer, an ionic liquid is used as a reaction solvent without using a conventional aromatic hydrocarbon solvent, thereby separating the acrylonitrile dimer in high purity and easily separating a phosphorus-based catalyst.

In addition, in the present invention, there are an ionic liquid, a product, and a catalyst in a lower portion of a second distillation column even at or above an acrylonitrile dimerization reaction temperature due to a low vapor pressure of the ionic liquid, whereby the product and the catalyst are present at low concentrations to effectively suppress a further reaction of the product to minimize loss of the product and the catalyst.

DESCRIPTION OF DRAWINGS

FIG. 1 is a process flow chart of a method of preparing an acrylonitrile dimer according to an exemplary embodiment of the present invention.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each apparatus and a fluid flow. In addition, the fluid may refer to a gas or a liquid.

Hereinafter, the present invention will be described in more detail with reference to the following FIG. 1 for better understanding of the present invention.

According to the present invention, a method of preparing an acrylonitrile dimer is provided.

A method of preparing an acrylonitrile dimer including: supplying an acrylonitrile monomer, a phosphorus-based catalyst, an alcohol solvent, and an ionic liquid to a reactor to perform a dimerization reaction to prepare a single-phase dimerization reaction product (S10); supplying a reactor discharge stream including the dimerization reaction product to a first distillation column, separating the alcohol solvent and an unreacted acrylonitrile monomer from an upper discharge stream, and supplying a lower discharge stream including an acrylonitrile dimer, the ionic liquid, and the phosphorus-based catalyst to a second distillation column (S20); and separating an upper discharge stream including the acrylonitrile dimer and separating a lower discharge stream including the ionic liquid and the phosphorus-based catalyst, from the second distillation column (S30), can be provided.

In the present invention, the term "product" may refer to a material to be obtained by a dimerization reaction, that is, an acrylonitrile dimer.

In the present invention, the term "reaction product" may refer to inclusion of both a product (acrylonitrile dimer) produced by the dimerization reaction of a reaction mixture and an unreacted reactant. For example, in a dimerization reaction of (S10), the reaction mixture may refer to an acrylonitrile monomer, a phosphorus-based catalyst, an alcohol solvent, and an ionic liquid, the product may refer to an acrylonitrile dimer, and the reaction product may include all of an acrylonitrile dimer (product), an unreacted acrylonitrile monomer, an alcohol solvent, an ionic liquid, and a phosphorus-based catalyst.

In the present invention, the term "single phase" may refer to a state in which, unlike an emulsion or colloid which undergoes phase separation such as floating material precipitation when being allowed to stand for a long time or being subjected to centrifugation, phase separation does not occur even when a mixture is allowed to stand for a long time or is subjected to centrifugation and has the same components and physicochemical properties in any extracted portion of the mixture. That is, the "single-phase dimerization reaction product" is a mixture in which an acrylonitrile dimer as a reaction product, an acrylonitrile monomer, a phosphorus-based catalyst, and alcohol are all dissolved in an ionic liquid, and may refer to a state in which the components and physicochemical properties are the same in any extracted portion of the mixture.

Meanwhile, for example, when water is used in the reaction mixture instead of alcohol, the phosphorus-based catalyst may react with water to be changed into an inactive state, and thus, it is preferred to use alcohol.

The acrylonitrile dimer, in particular, a linear acrylonitrile dimer, is used as an intermediate for synthesizing hexamethylenediamine (HMDA) which is a main monomer of Nylon 66 or used for preparation of a waterproof agent, a vulcanization accelerator, and the like.

Conventionally, the acrylonitrile dimer was obtained by dimerizing an acrylonitrile monomer in the presence of a catalyst. Specifically, the acrylonitrile monomer was dimerized using a ruthenium (Ru)-based compound, a cobalt (Co)-based compound, a phosphorus (P)-based compound, or the like as a catalyst, thereby preparing an acrylonitrile dimer.

Among the catalysts used in preparing the acrylonitrile dimer, particularly, a phosphorus-based catalyst, has excellent reactivity and selectivity, and the acrylonitrile dimer was prepared by a method of adding acrylonitrile to a mixed solvent including an alcohol solvent as a proton donating solvent and an inert solvent such as an aromatic hydrocarbon solvent as a reaction solvent and performing a dimerization reaction using the catalyst.

However, in the above method, due to an azeotropic problem between an alcohol solvent and an aromatic hydrocarbon solvent and between an acrylonitrile monomer and an aromatic hydrocarbon solvent, when the alcohol solvent, the aromatic hydrocarbon solvent, and the acrylonitrile monomer are recycled, impurities and low-boiling point by-products in the recycled unreacted acrylonitrile monomers are accumulated so that it is difficult to maintain a reaction condition, and thus, in order to prevent the accumulation of impurities and by-products, a process step for purging is added or a yield of the acrylonitrile dimer is decreased due to the accumulation of impurities and by-products.

In addition, separation of the phosphorus-based catalyst, the acrylonitrile dimer, and the mixed solvent is performed by a distillation method and the distillation method is a method of separating a catalyst by applying heat using the characteristic of the phosphorus-based catalyst having a higher boiling point than a reaction product or a product, and when the catalyst is separated from the acrylonitrile dimerization reaction product by the distillation method, the thermal decomposition and the side reaction of acrylonitrile dimerization products proceeds due to a high temperature condition to produce oligomers of thermal decomposition products of the acrylonitrile dimer, trimer, polymer, or higher, thereby decreasing a yield of the acrylonitrile dimer.

Regarding this, in the preparation of the acrylonitrile dimer in the present invention, the ionic liquid is used as a reaction solvent instead of a conventional aromatic hydrocarbon solvent, thereby providing a method which does not add an unnecessary process step to increase process efficiency, increases a yield of the acrylonitrile dimer, separates the acrylonitrile dimer in high purity, and improves a recycling rate of the phosphorus-based catalyst.

According to an exemplary embodiment of the present invention, (S10) can be a step of supplying an acrylonitrile monomer, a phosphorus-based catalyst, an alcohol solvent, and an ionic liquid to a reactor 100 to perform a dimerization reaction to prepare an acrylonitrile dimer.

According to an exemplary embodiment of the present invention, in (S10), the acrylonitrile dimerization reaction can be performed by a common method known in the art. For example, an appropriate amount of a raw material is supplied to the reactor 100 and an acrylonitrile dimerization reaction can be performed in an optimal temperature range and an optimal pressure range.

For example, the acrylonitrile dimerization reaction can be performed in a temperature range of 0° C. to 100° C. and a pressure range of 1 bar to 10 bar. When the acrylonitrile dimerization reaction is performed in the temperature range and the pressure range, the acrylonitrile dimer can be prepared in an excellent conversion rate.

According to an exemplary embodiment of the present invention, the phosphorus-based catalyst can be represented by the following Chemical Formula 1:

[Chemical Formula 1]

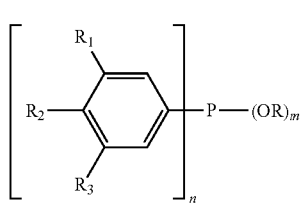

wherein

R represents an alkyl group having 1 to 5 carbon atoms, an aryl group having 6 to 12 carbon atoms, or a cycloalkyl group having 3 to 8 carbon atoms, each of $R_1$ to $R_3$ represents hydrogen, an alkyl group, an amino group, or an alkoxy group having 1 to 5 carbon atoms, and n and m are independently an integer of 1 to 2.

As a specific example, the phosphorus-based catalyst can be represented by the following Chemical Formula 1-1:

[Chemical Formula 1-1]

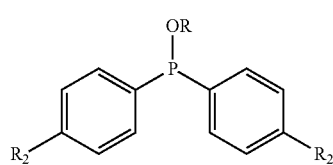

wherein

R is a methyl group, an ethyl group, an isopropyl group, or a cyclohexyl group, and $R_2$ is hydrogen, a methyl group, or an ethyl group.

As a more specific example, the phosphorus-based catalyst can be represented by the following Chemical Formula 1-2:

[Chemical Formula 1-2]

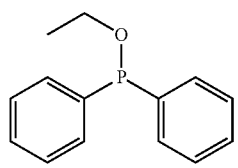

According to an exemplary embodiment of the present invention, the alcohol solvent can include, for example, one or more selected from the group consisting of isopropyl alcohol, methyl alcohol, and cyclohexyl alcohol. As a specific example, the alcohol solvent can be isopropyl alcohol.

According to an exemplary embodiment of the present invention, the ionic liquid includes cations and anions, and since the nature of these cations and anions can be changed to easily adjust the physical and chemical properties thereof, the ionic liquid is widely used in various fields.

In the ionic liquid, the cations can include one or more selected from the group consisting of pyridinium-based cations, imidazolium-based cations, pyrrolidinium-based cations, ammonium-based cations, and phosphonium-based cations.

The pyridinium-based cation can include, for example, one or more selected from the group consisting of a 1-butyl-2-methylpyridinium cation, a 1-butyl-3-methylpyridinium cation, a butylmethylpyridinium cation, a 1-butyl-4-dimethylacetylpyridinium cation, a 1-butyl-4-methylpyridinium cation, a 1-ethyl-2-methylpyridinium cation, a 1-ethyl-3-methylpyridinium cation, a 1-ethyl-4-dimethylacetylpyridinium cation, a 1-ethyl-4-methylpyridinium cation, a 1-hexyl-4-dimethylacetylpyridinium cation, a 1-hexyl-4-methylpyridinium cation, a 1-octyl-3-methylpyridinium cation, a 1-octyl-4-methylpyridinium cation, a 1-propyl-3-methylpyridinium cation, a 1-propyl-4-methylpyridinium cation, a butylpyridinium cation, an ethylpyridinium cation, a heptylpyridinium cation, a hexylpyridinium cation, a hydroxypropylpyridinium cation, an octylpyridinium cation, a pentylpyridinium cation, and a propylpyridinium cation.

In addition, the imidazolium-based cation can include, for example, one or more selected from the group consisting of a butylethylimidazolium cation, a butylmethylimidazolium cation, a butyldimethylimidazolium cation, a decaethylimidazolium cation, a decamethylimidazolium cation, a diethylimidazolium cation, a dimethylimidazolium cation, an ethyl-2,4-dimethylimidazolium cation, an ethyldimethylimidazolium cation, an ethylimidazolium cation, an ethylmethylimidazolium cation, an ethylpropylimidazolium cation, an ethoxyethylmethylimidazolium cation, an ethoxydimethylimidazolium cation, a hexadecylmethylimidazolium cation, a heptylmethylimidazolium cation, a hexylethylimidazolium cation, a hexylmethylimidazoliumcation, a hexyldimethylimidazolium cation, a methoxyethylmethylimidazolium cation, a methoxypropylmethylimidazolium cation, a methylimidazolium cation, a dimethylimidazolium cation, a methylnonylimidazolium cation, an octadecylmethylimidazolium cation, a hydroxyethylmethylimidazolium cation, a hydroxyloctylmethylimidazolium cation, a hydroxylpropylmethylimidazolium cation, an octylmethylimidazolium cation, an octyldimethylimidazolium cation, a phenylethylmethylimidazolium cation, a phenylmethylimidazolium cation, a phenyldimethylimidazolium cation, a pentylmethylimidazolium cation, and a propylmethylimidazolium cation.

In addition, the pyrrolidinium-based cation can include, for example, one or more selected from the group consisting of a butylmethylpyrrolidinium cation, a butylpyrrolidinium cation, a hexylmethylpyrrolidinium cation, a hexylpyrrolidinium cation, an octylmethylpyrrolidinium cation, an octylpyrrolidinium cation, and a propylmethylpyrrolidinium cation.

In addition, the ammonium-based cation can include, for example, one or more selected from the group consisting of a butylammonium cation, a tributylammonium cation, a tetrabutylammonium cation, a butylethyldimethylammonium cation, a butyltrimethylammonium cation, a N,N,N-trimethylethanolammonium cation, an ethylammonium cation, a diethylammonium cation, a tetraethylammonium cation, a tetraheptylammonium cation, a tetrahexylammonium cation, a methylammonium cation, a dimethylammonium cation, a tetramethylammonium cation, an ammonium cation, a but yldimethylethanolammonium cation, a dimethylethanolammonium cation, an ethanolammonium cation, an ethyldimethylethanolammonium cation, a tetrapentylammonium cation, and a tetrapropylammonium cation.

In addition, the phosphonium-based cation can include, for example, one or more selected from the group consisting of a tetrabutylphosphonium cation and tributyloctylphosphonium cation.

Specifically, in the an ionic liquid, the cation can include a pyridinium-based cation, and more specifically, the pyridinium-based cation can be one or more selected from the group consisting of a 1-butyl-4-methylpyridinium cation and a 1-ethyl-3-methylpyridinium cation.

In the ionic liquid, the anion can include one or more selected from the group consisting of a bis(trifluoromethanesulfonyl)amide anion, a hexafluorophosphate anion, a trifluoromethanesulfonate anion, a dicyanamide anion, a tetrafluoroborate anion, a thiocyanate anion, a nitrate anion, a sulfonate anion, an ethylsulfate anion, and a trifluoroacetate anion. Specifically, in the anionic liquid, the anion can include a tetrafluoroborate anion or an ethylsulfonate anion.

More specifically, the ionic liquid can include one or more selected from the group consisting of 1-butyl-4-methylpyridinium tetrafluoroborate and 1-ethyl-3-methylpyridinium ethylsulfate.

The ionic liquid can have a vapor pressure of 0.003 Pa or less as measured at a temperature of 100° C. For example, the vapor pressure measured at a temperature of 100° C. can be 0.0001 Pa to 0.003 Pa, 0.0005 Pa to 0.003 Pa, or 0.001 Pa to 0.003 Pa. As such, the ionic liquid having a very low vapor pressure is used in the acrylonitrile dimerization reaction as a solvent, thereby minimizing loss of the product and the catalyst.

Specifically, the ionic liquid having a very low vapor pressure is used, whereby there are the ionic liquid, the product, and the catalyst in a lower portion of the second distillation column 300 even at or above an acrylonitrile dimerization reaction temperature, and thus, the product and the catalyst are present at low concentrations to effectively suppress a further reaction of the product to minimize loss of the product and the catalyst.

Meanwhile, for example, when an aromatic hydrocarbon solvent representing a vapor pressure of 1000 Pa or more at a temperature of 100° C. is used instead of the ionic liquid, a flow rate of the aromatic hydrocarbon solvent separated from an upper portion of the second distillation column 300 is increased at or above the acrylonitrile dimerization reaction temperature, and thus, the product and the catalyst are present at high concentrations in the lower portion of the second distillation column 300, and due to a further reaction of the product, loss of the catalyst can occur and a yield of the acrylonitrile dimer as the product can be decreased.

Specifically, the phosphorus-based catalyst can be a catalyst in an active state and is converted into an inactive state by a further reaction occurring in the lower portion of the second distillation column 300, thereby causing loss of the catalyst.

In (S10), the ionic liquid can be subjected to a step of removing moisture and then be supplied to the reactor. For example, the step of removing moisture of the ionic liquid can include: mixing the ionic liquid and a second solvent to prepare a mixed solution; adding a porous material to the mixed solution to remove moisture; and separating the ionic liquid from the mixed solution.

The second solvent used in the step of removing moisture of the ionic liquid can be a material having compatibility with the ionic liquid and also low boiling point and viscosity. Specifically, the second solvent used in the step of removing moisture of the ionic liquid can be appropriately selected depending on the kind of the ionic liquid, and for example, the second solvent can include one or more selected from the group consisting of ethyl acetate, alkyl acetate, ketone, alcohol, and acetonitrile.

The porous material can include one or more selected from the group consisting of molecular sieves and zeolite which are commonly used in the art. When the porous material as such is added to the mixed solution and allowed to stand for a certain period of time, the porous material can absorb the moisture to remove the moisture.

The step of separating the ionic liquid from the mixed solution from which the moisture is removed using the porous material can be performed by an evaporation method by heating. As such, when the mixed solution is heated, the ionic liquid having a low vapor pressure is not evaporated and only the second solvent is evaporated, thereby easily separating the ionic liquid. The heating temperature can be, for example, 25° C. to 200° C., 25° C. to 150° C., or 25° C. to 100° C. In addition, upon the evaporation by heating, the pressure can be 100 mbar or less, 0.01 mbar to 100 mbar, or 0.1 mbar to 50 mbar. The second solvent is evaporated by the heating under the temperature and reduced pressure condition, thereby effectively separating the ionic liquid.

The ionic liquid can have a moisture content of 50 ppm or less. For example, the moisture content contained in the ionic liquid can be 1 ppm to 50 ppm, 1 ppm to 30 ppm, or 1 ppm to 15 ppm, or can hardly contain moisture. The ionic liquid having the moisture content within the range is used, thereby preventing oxidation of the catalyst to improve a conversion rate and a selectivity in the acrylonitrile dimerization reaction.

According to an exemplary embodiment of the present invention, in the preparation of the acrylonitrile dimer, the mixed solvent includes an alcohol solvent and the ionic liquid, thereby improving the yield of the acrylonitrile dimer. Specifically, in the present invention, the ionic liquid is used instead of the aromatic hydrocarbon solvent, thereby improving the yield of the acrylonitrile dimer as compared with the case of using the conventional mixed solvent of an aromatic hydrocarbon solvent and an alcohol solvent. More specifically, conventionally, when the content of the alcohol solvent in the mixed solvent was lowered, a reaction rate was decreased so that production of a by-product was increased to decrease the yield of the acrylonitrile dimer, and when the content of the alcohol solvent was increased, a reaction rate was increased, but production of a by-product was increased to decrease the yield of the acrylonitrile dimer. Regarding this, in the present invention, a mixed solvent including the alcohol solvent and the ionic liquid is used, thereby solving the conventional problem described above.

A volume ratio of the alcohol solvent and the ionic liquid supplied to the reactor 100 can be 1:5 to 20. For example, the volume ratio of the alcohol solvent and the ionic liquid can be 1:5 to 18, 1:5 to 15, or 1:8 to 13. In the acrylonitrile dimerization reaction, the alcohol solvent and the ionic liquid are mixed at a volume ratio within the range and used as a reaction solvent, thereby suppressing production of a by-product to improve the yield of the acrylonitrile dimer. As a specific example, when the volume ratio of the alcohol solvent and the ionic liquid is 1:5 or more, it may be prevented that reactivity of the phosphorus-based catalyst is excessively increased to produce an oligomer, and when the volume ratio is 1:20 or less, a decrease of the reaction rate is prevented to improve productivity.

In (S10), the acrylonitrile dimerization reaction product can be produced by the acrylonitrile dimerization reaction.

Specifically, the acrylonitrile dimerization reaction product can include the acrylonitrile dimer, an unreacted acrylonitrile monomer, the alcohol solvent, the phosphorus-based catalyst, and the ionic liquid.

According to an exemplary embodiment of the present invention, (S20) can be a step of supplying the acrylonitrile dimerization reaction product produced by the acrylonitrile dimerization reaction in (S10) to the first distillation column 200 to separate the alcohol solvent and the unreacted acrylonitrile monomer from the upper discharge stream and supplying the lower discharge stream including the acrylonitrile dimer, the ionic liquid, and the phosphorus-based catalyst to the second distillation column 300.

In (S20), an operating temperature of the first distillation column 200 can be 10° C. to 60° C., 10° C. to 50° C., or 15° C. to 40° C. In addition, in (S20), the operating pressure of the first distillation column 200 can be 1 mbar to 200 mbar, 1 mbar to 80 mbar, or 1 mbar to 40 mbar. As such, in (S20), the operating temperature and the operating pressure of the first distillation column 200 is controlled within the range, whereby the acrylonitrile monomer and the alcohol solvent can be selectively evaporated without evaporating the phosphorus-based catalyst, the acrylonitrile dimer, and the ionic liquid to separate the acrylonitrile monomer and the alcohol solvent from an upper portion of the first distillation column 200.

According to an exemplary embodiment of the present invention, (S30) can be a step for separating the upper discharge stream including the acrylonitrile dimer and the lower discharge stream including the phosphorus-based catalyst and the ionic liquid, respectively, from the lower discharge stream of the first distillation column 200 in (S20).

Specifically, in (S20), the lower discharge stream from the first distillation column 200 is supplied to the second distillation column 300, the acrylonitrile dimer is separated from the upper discharge stream in the second distillation column 300, and a mixture of the phosphorus-based catalyst and the ionic liquid can be separated as the lower discharge stream.

In (S30), an operating temperature of the second distillation column 300 can be 100° C. to 200° C., 100° C. to 180° C., or 100° C. to 150° C. In addition, in (S30), the operating pressure of the second distillation column 300 can be 0.005 mbar to 80 mbar, 0.005 mbar to 25 mbar, or 0.01 mbar to 6 mbar. As such, the operating temperature and the operating pressure of the second distillation column 300 are controlled within the range in (S30), thereby selectively evaporating the acrylonitrile dimer to separate the acrylonitrile dimer from the upper discharge stream from the second distillation column 300.

In (S30), the acrylonitrile dimer separated from the upper portion of the second distillation column can include a linear acrylonitrile dimer including 1,4-dicyanobutene which can be converted into adiponitrile. In addition, a selectivity of the linear acrylonitrile dimer in the acrylonitrile dimers separated from the upper discharge stream from the second distillation column 300 in (S30) can be 90% or more. In addition, the phosphorus-based catalyst and the ionic liquid which are not separated from the upper portion of the second distillation column 300 in (S30) can be separated from the lower portion of the second distillation column 300.

According to an exemplary embodiment of the present invention, a ratio of a content of the phosphorus-based catalyst separated in (S30) to a content of the phosphorus-based catalyst supplied to the reactor 100 in (S10) can be 0.5 to 0.95, 0.60 to 0.95, or 0.80 to 0.95. As such, in the method of preparing an acrylonitrile dimer according to the present invention, the ionic liquid is used as a reaction solvent, thereby preventing a further reaction of the acrylonitrile dimer and the catalyst in the lower portion of the second distillation column 300 to improve a recycling rate of the phosphorus-based catalyst to the range described above.

After (S30), in a remaining mixture in the second distillation column 300, the ionic liquid can be present together with the acrylonitrile dimer and the phosphorus-based catalyst. As such, the ionic liquid is used as a reaction solvent in the preparation of the acrylonitrile dimer, whereby the ionic liquid is present in the lower portion of the second distillation column 300 together with the acrylonitrile dimer and the phosphorus-based catalyst without being evaporated by distillation, thereby minimizing production of an acrylonitrile oligomer and a polymer due to a further reaction of the acrylonitrile dimer and the phosphorus-based catalyst.

According to an exemplary embodiment of the present invention, in the method of preparing an acrylonitrile dimer, a distillation column (not shown), a condenser (not shown), a reboiler (not shown), a pump (not shown), a compressor (not shown), a mixer (not shown), a separator (not shown) and the like can be further installed, if necessary.

Hereinabove, the method of preparing an acrylonitrile dimer according to the present invention has been described and illustrated in the drawings; however, the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for carrying out the method of preparing an acrylonitrile dimer according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES

Example 1

As shown in the process flow chart illustrated in FIG. 1, 0.6 mL of an acrylonitrile monomer (AN), 98.9 μL of a phosphorus-based catalyst of the following Chemical Formula 1-2 (Sigma Aldrich, ethyl diphenylphosphinite), 0.2 mL of isopropyl alcohol (IPA, 99.5%), and 2 mL of 1-butyl-4-methylpyridinium tetrafluoroborate having a moisture content of about 3000 ppm (Tokyo Chemical Industry Co., Ltd., 98%) as an ionic liquid were supplied to a reactor 100, and an acrylonitrile dimerization reaction was performed at a temperature of 60° C. for 24 hours to obtain an acrylonitrile dimerization reaction product.

The moisture content of the ionic liquid was measured using a Karl-Fischer titrator (Metrohm 917 Coulometer) and a HYDRANAL reagent. First, a measurement cell in the Karl-Fischer titrator was filled with 100 mL of a HYDRANAL Coulomat AG solution. A pretreatment was performed to decrease a drift (an appropriate amount of moisture per minute) down to 20 μg/min, and allowed to stand until the numerical value is stabilized. The ionic liquid was collected in an environment having a minimized outside air contact and was weighed in a scale. The ionic liquid collected with a syringe was added to a cell which had been pretreated, the syringe was weighed, and moisture titration was performed. When the drift over time reached a drift just before sample addition, the titration was finished. At this time, the weight of the ionic liquid ($m_{IL}$), a drift just before sample addition ($W_i$), a drift over time measured during sample titration ($W(t)$), and a measurement time (t) were confirmed to calculate a moisture content (c) in the ionic liquid by the following Equation 1. When the sample is added to the measurement cell too slowly, an error due to the moisture introduced during sample addition may be increased, and thus, measurement was performed carefully.

$$\frac{\int_0^t W(t)dt - W_i \times t}{m_{IL}} \quad \text{[Equation 1]}$$

[Chemical Formula 1-2]

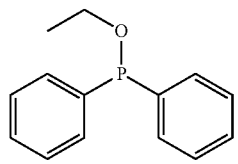

Then, the acrylonitrile dimerization reaction product was supplied to a first distillation column 200, and the first distillation column 200 was controlled to a temperature of 40° C. and a pressure of 40 mbar to separate an acrylonitrile monomer and isopropyl alcohol as a low boiling-point material from an upper discharge stream from the first distillation column 200.

Then, the lower discharge stream from the first distillation column 200 was supplied to a second distillation column 300, an acrylonitrile dimer was separated from an upper discharge stream from the second distillation column 300 while a temperature of the second distillation column 300 was controlled to 100° C. to 150° C. and a pressure thereof was reduced to 6 mbar or less, and the ionic liquid and the phosphorus-based catalyst were separated from the lower discharge stream. At this time, it was confirmed that the acrylonitrile dimer included 1,4-dicyanobutene.

Example 2

The process was performed in the same manner as in Example 1, except that 1-butyl-4-methylpyridinium tetrafluoroborate, which had a moisture content of 10 ppm, obtained by, before being supplied to the reactor 100, being mixed with 6 mL of ethyl acetate, adding 2 g of a molecular sieve (DAEJUNG CHEMICALS & METALS CO., LTD., Molecular sieve 4 A 4-8 mesh beads), being allowed to stand for 48 hours, and reducing the pressure to 1 mbar to evaporate ethyl acetate, was used.

Comparative Example

Comparative Example 1

As shown in the process flow chart illustrated in FIG. 1, 0.6 mL of the acrylonitrile monomer (AN), 98.9 μL of the phosphorus-based catalyst of Chemical Formula 1-2, 0.2 mL of isopropyl alcohol (IPA, ≥99.5%), and 2 mL of toluene (Tol, ≥99.8%) were supplied to the reactor 100, and the acrylonitrile dimerization reaction was performed at a temperature of 60° C. for 24 hours to obtain an acrylonitrile dimerization reaction product.

Then, the acrylonitrile dimerization reaction product was supplied to a first distillation column 200, and the first distillation column 200 was controlled to a temperature of 40° C. and a pressure of 40 mbar to separate the acrylonitrile monomer and isopropyl alcohol and a part of toluene as a low boiling-point material from an upper discharge stream from the first distillation column 200.

Then, the lower discharge stream from the first distillation column 200 was supplied to a second distillation column 300, toluene and the acrylonitrile dimer were separated from the upper discharge stream from the second distillation column 300 while the temperature of the second distillation column 300 was controlled to 100° C. to 150° C. and the pressure thereof was reduced to 6 mbar or less, and the phosphorus-based catalyst was separated from the lower discharge stream. At this time, it was confirmed that the acrylonitrile dimer included 1,4-dicyanobutene.

Experimental Examples

Experimental Example 1

A conversion rate into the acrylonitrile dimer and a selectivity of the linear acrylonitrile dimer (linear selectivity) for the acrylonitrile dimerization reaction products according to Examples 1 and 2 and Comparative Example 1 were analyzed by gas chromatography (GC). Specifically, since in Examples 1 and 2, a large amount of the ionic liquid having a very low vapor pressure was included in the acrylonitrile dimerization reaction product to deteriorate stability of a GC analysis column, when phase separation occurred after mixing 1 mL of the acrylonitrile dimerization reaction product and 3 mL of toluene, a supernatant (toluene phase) was collected and analyzed. In addition, the acrylonitrile dimerization reaction product in Comparative Example 1 was subjected to GC analysis as it was. The analysis method was as follows, and the results are shown in the following Table 1.

GC analysis: GC-FID was used to perform quantitative analysis of the mass of each component included in a constant mass sample. Here, the kind of component was identified depending on a retention time of a peak shown while the temperature of the column was raised from 40° C. to 280° C. and a peak area was converted into the mass of the component.

Conversion rate (%): A reduction rate of the mass of the acrylonitrile monomer after the acrylonitrile dimerization reaction ($m_{AN,t}$) as compared with the mass of the acrylonitrile monomer before the reaction ($m_{AN,t0}$) was measured by the following Equation 2:

$$(m_{AN,t0} - m_{AN,t})/m_{AN,t0} \times 100 \quad \text{[Equation 2]}$$

Linear selectivity: A fraction of the mass of 1,4-dicyanobutene ($m_{DCB}$) which is a linear product of the total mass of the acrylonitrile dimer ($m_{DCB} + m_{MGN}$) was measured by the following Equation 3:

$$m_{DCB}/(m_{DCB} + m_{MGN}) \times 100 \quad \text{[Equation 3]}$$

TABLE 1

|  | Example 1 | Example 2 | Comparative Example 1 |
|---|---|---|---|
| Conversion rate (%) | 40.6 | 54 | 75.2 |
| Linear selectivity (%) | 96 | 94 | 96 |

Referring to Table 1, in Example 1 using the ionic liquid as the reaction solvent like the present invention, it was confirmed that the selectivity to the linear acrylonitrile dimer was equivalent to superior as compared with conventional Comparative Example 1 using toluene.

In addition, in Example 2 using the ionic liquid having a low content of moisture as the reaction solvent, it was confirmed that the conversion rate was slightly increased.

Experimental Example 2

The acrylonitrile dimer content and the active phosphorus-based catalyst and oligomer content in Example 1 and Comparative Example 1 were measured by the following method and are shown in the following Table 2.

Method of measuring acrylonitrile dimer content: A product obtained from the upper portion of the second distillation column was weighed, and GC-FID was used to measure the content of the acrylonitrile dimer included in the sample.

Method of measuring active phosphorus-based catalyst and oligomer content: In Example 1, the product obtained from the lower portion of the second distillation column was weighed, toluene was added to cause phase separation, and then a supernatant, a lower layer solution, and a solid were weighed, respectively. Then, the content of the phosphorus-based catalyst and the oligomer (including trimer and tetramer) in the supernatant was measured using GC-FID. In addition, in Comparative Example 1, the product obtained from the lower portion of the second distillation column was weighed and toluene was added to dissolve the product. Then, an undissolved material was separated by a filter, dried, and weighed. Then, the content of the phosphorus-based catalyst and the oligomer (including trimer and tetramer) in the toluene solution was measured using GC-FID.

TABLE 2

|  | Example 1 | Example 2 | Comparative Example 1 |
|---|---|---|---|
| Acrylonitrile dimer content (g) in product obtained in upper portion of second distillation column | 0.116 | 0.156 | 0.087 |
| Acrylonitrile dimer content (g) in product obtained in lower portion of second distillation column | 0.034 | 0.050 | 0.01 |
| Active phosphorus-based catalyst (%) | 60 | 80 | 40 |
| Oligomer content (g) | 0.030 | 0.050 | 0.241 |

Referring to Table 2, in Examples 1 and 2 using the ionic liquid as the reaction solvent like the present invention, it was confirmed that the finally obtained content of the acrylonitrile dimer was increased by about 1.5 times to twice or more as compared with that of conventional Comparative Example 1 using toluene. The results are due to the fact that in Comparative Example 1, toluene was used instead of the ionic liquid and toluene was included together with the acrylonitrile dimer in the upper discharge stream of the second distillation column 300 due to azeotropy of toluene and the acrylonitrile dimer.

In addition, in Examples 1 and 2, it was confirmed that the active phosphorus-based catalyst obtained from the lower portion of the second distillation column 300 was 60% to 80% or more relative to the amount added to the acrylonitrile dimerization reaction, which was increased by about 1.5 times to twice or more as compared with that of Comparative Example 1. This is because in Comparative Example 1, the phosphorus-based catalyst in an active state was converted into an inactive state in the process of forming the oligomer by the further reaction of the acrylonitrile dimer and the phosphorus-based catalyst in the lower portion of the second distillation column 300 due to the absence of the ionic liquid.

Thus, it was found that in the present invention, the ionic liquid was used as the reaction solvent of the acrylonitrile dimerization reaction, thereby increasing an amount of obtaining the acrylonitrile dimer and improving the recycling rate of the phosphorus-based catalyst.

In addition, it was confirmed that in Examples 1 and 2, the ionic liquid was present together with the acrylonitrile dimer and the phosphorus-based catalyst in the lower portion of the second distillation column 300 to prevent a continuous reaction of the acrylonitrile dimer and the phosphorus-based catalyst, thereby suppressing production of an oligomer and a polymer.

In comparison, it was confirmed that in Comparative Example 1, the acrylonitrile dimer and the phosphorus-based catalyst were present at high concentrations without the ionic liquid in the lower portion of the second distillation column 300, so that the content of the acrylonitrile dimer was decreased as compared with Example 1 by the further reaction of the acrylonitrile dimer and the phosphorus-based catalyst, and the oligomer was formed about 4.8 times to 8 times or more, and thus, most of the remaining mixture was the oligomer.

The invention claimed is:

1. A method of preparing an acrylonitrile dimer, the method comprising:
supplying an acrylonitrile monomer, a phosphorus-based catalyst, an alcohol solvent, and an ionic liquid to a reactor to perform a dimerization reaction to prepare a single-phase dimerization reaction product (S10);
supplying a reactor discharge stream including the dimerization reaction product to a first distillation column, separating the alcohol solvent and an unreacted acrylonitrile monomer from an upper discharge stream, and supplying a lower discharge stream including an acrylonitrile dimer, the ionic liquid, and the phosphorus-based catalyst to a second distillation column (S20); and
separating an upper discharge stream including the acrylonitrile dimer and separating a lower discharge stream including the ionic liquid and the phosphorus-based catalyst, from the second distillation column (S30),
wherein the ionic liquid includes a cation and an anion, and the ionic liquid includes the pyridinium-based cation as the cation and the tetrafluoroborate anion as the anion, and
wherein a moisture content in the ionic liquid is 50 ppm or less.

2. The method of preparing an acrylonitrile dimer of claim 1, wherein the phosphorus-based catalyst is represented by Chemical Formula 1:

[Chemical Formula 1]

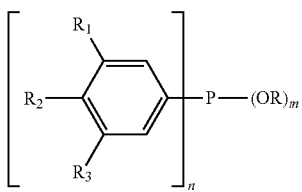

wherein,
R represents an alkyl group having 1 to 5 carbon atoms, an aryl group having 6 to 12 carbon atoms, or a cycloalkyl group having 3 to 8 carbon atoms,
each of $R_1$ to $R_3$ represents hydrogen, an alkyl group having 1 to 5 carbon atoms, an amino group, or an alkoxy group, respectively, and
n and m are independently an integer of 1 to 2.

3. The method of preparing an acrylonitrile dimer of claim 1, wherein the alcohol solvent includes one or more alcohols selected from the group consisting of isopropyl alcohol, methyl alcohol, and cyclohexyl alcohol.

4. The method of preparing an acrylonitrile dimer of claim 1, wherein the pyridinium-based cation includes one or more selected from the group consisting of 1-butyl-4-methylpyridinium and 1-ethyl-3-methylpyridinium.

5. The method of preparing an acrylonitrile dimer of claim 1, wherein a volume ratio of the alcohol solvent and the ionic liquid supplied to the reactor is 1:5 to 20.

6. The method of preparing an acrylonitrile dimer of claim 1, wherein in (S10), the ionic liquid is subjected to removing moisture and then is supplied to the reactor.

7. The method of preparing an acrylonitrile dimer of claim 1, wherein in the step (S20), an operating temperature of the first distillation column is 10° C. to 60° C. and an operating pressure of the first distillation column is 1 mbar to 200 mbar.

8. The method of preparing an acrylonitrile dimer of claim 1, wherein in the step (S30), an operating temperature of the second distillation column is 100° C. to 200° C. and an operating pressure of the second distillation column is 0.005 mbar to 80 mbar.

9. The method of preparing an acrylonitrile dimer of claim 1, wherein a ratio of a content of the phosphorus-based catalyst separated in the step (S30) to a content of the phosphorus-based catalyst supplied to the reactor in the step (S10) is 0.5 to 0.95.

* * * * *